United States Patent
Chou

(10) Patent No.: US 8,644,915 B2
(45) Date of Patent: Feb. 4, 2014

(54) HANDHELD ELECTROCARDIOGRAPHIC DEVICE

(75) Inventor: Chang-An Chou, Taipei (TW)

(73) Assignee: MD Biomedical, Inc., Taipei (TW)

( * ) Notice: Subject to any disclaimer, the term of this patent is extended or adjusted under 35 U.S.C. 154(b) by 0 days.

(21) Appl. No.: 13/383,840

(22) PCT Filed: Jul. 14, 2010

(86) PCT No.: PCT/CN2010/001061
§ 371 (c)(1),
(2), (4) Date: Jan. 13, 2012

(87) PCT Pub. No.: WO2011/006356
PCT Pub. Date: Jan. 20, 2011

(65) Prior Publication Data
US 2012/0116240 A1    May 10, 2012

(30) Foreign Application Priority Data
Jul. 14, 2009  (CN) .......................... 2009 1 0158564

(51) Int. Cl.
*A61B 5/0404* (2006.01)
(52) U.S. Cl.
USPC .......................... 600/509; 600/523
(58) Field of Classification Search
USPC ................................. 600/523, 509
See application file for complete search history.

(56) References Cited

U.S. PATENT DOCUMENTS

| | | | | |
|---|---|---|---|---|
| 4,535,783 | A * | 8/1985 | Marangoni | 600/524 |
| 6,587,712 | B1 | 7/2003 | Itoh | |
| 2006/0047210 | A1* | 3/2006 | Moroki et al. | 600/509 |
| 2007/0197929 | A1* | 8/2007 | Porath et al. | 600/523 |

FOREIGN PATENT DOCUMENTS

| | | | |
|---|---|---|---|
| CN | 1564565 | A | 1/2005 |
| CN | 1739447 | A | 3/2006 |
| CN | 2785540 | Y | 6/2006 |
| CN | 1923136 | A | 3/2007 |
| CN | 201127603 | Y | 10/2008 |
| WO | 8102832 | A1 | 10/1981 |
| WO | 8706447 | A1 | 11/1987 |

* cited by examiner

*Primary Examiner* — Christopher D Koharski
*Assistant Examiner* — Michael Carey

(57) ABSTRACT

A handheld electrocardiographic device for perform an ECG signal acquisition is provided. The ECG device includes at least two electrodes for obtaining ECG signals from a user's skin, an analog signal processing module, an analog/digital converter for digitizing the ECG signals, a processor, which controls the ECG device and processes the ECG signals, a display unit for displaying a processed result of ECG signals and other related information, a memory for data storage, a battery for providing power, at least a contacting interface having at least one of the electrodes mounted thereon, and a detecting unit for sensing a physical condition of the contacting interface, wherein the processor compares the physical condition to a preset criterion, and takes the result as a reference for processing the ECG signals.

20 Claims, 4 Drawing Sheets

HANDHELD ELECTROCARDIOGRAPHIC DEVICE

FIELD OF THE INVENTION

The present invention is related to a handheld electrocardiographic (ECG) device, and more particularly, to a handheld ECG device with improved operation procedure and data reliability.

BACKGROUND OF THE INVENTION

As known, electrocardiography is a very useful tool to diagnose heart diseases, for example, arrhythmia, cardiac hypertrophy, myocardial infarction, coronary insufficiency, or angina pectoris.

Generally, the user can take the ECG examination in the hospital or at home. The ECG system used in the hospital provides comprehensive and accurate information with multi-lead (e.g., complete 12-lead) and/or long-term monitoring. On the other hand, the ECG Holter, which can be carried with the user, has a smaller volume for facilitating a 24-hour or longer ECG recording, this is particularly important for some diseases whose occurrences are unpredictable.

Afterward, a handheld ECG device is developed which is designed as compact and portable to perform a heart examination or ECG recording when needed. As using this kind of ECG device, the examination/recording can be easily performed by simply contacting the electrodes with the user's skin (hands and/or torso). Therefore, through this quick and convenient examination/recording, the user can check the heart situation due to the doctor's direction or the occurrence of uncomfortableness.

FIG. 1 shows a common handheld ECG device 100, including a main body 101, a display 102 and an operation interface 103. The main body 101 includes a first surface 1011 with a first electrode 104 mounted thereon and a second surface 1012 with a second electrode 105 mounted thereon. As using, after being switched on through the operation interface 103, the first electrode 104 should be contacted with the right hand of the user and the second electrode 105 should be contacted with the left hand or the torso at the left side. Then, by pressing the "START" button, the examination/recording starts lasting for a predetermined period of time. Finally, the result is shown on the display 102.

It is obvious that, as using the above-mentioned ECG device, the success of the examination/recording relies on the contact between the electrodes and the skin, that is, a certain level of force should be applied during the period to ensure a stable and workable contact. However, since the conventional ECG device does not indicate any relative information about the electrode contact or the force applied, the user might doubt that if a proper contact between the electrode and the skin is achieved. Accordingly, the user may question the accuracy of the result and further distrust it.

Therefore, for this kind of ECG device, it always happens that the user starts the examination/recording with an insufficient and/or unstable force application to cause an incorrect result, or the user, due to the fear of failure, nervously applies an excess level of force for achieving the contact so as to cause a mental stress or muscular pain.

Consequently, the object of the present invention is to provide a handheld ECG device which can provide the user a definite indication of the contact between the electrode and the skin during the examination/recording so as to increase the possibility of success.

Another object of the present invention is to provide a handheld ECG device which not only can remind the user if a proper contact for performing the examination/recording is achieved, but also can indicate the user the initiation, interruption and/or termination thereof, thereby contributing to the improvement of data accuracy and reliability.

SUMMARY OF THE INVENTION

According to one aspect of the present invention, a handheld electrocardiographic device for perform an ECG signal acquisition is provided. The ECG device includes at least two electrodes for obtaining ECG signals from a user's skin, an analog signal processing module, an analog/digital converter for digitizing the ECG signals, a processor, which controls the ECG device and processes the ECG signals, a display unit for displaying a processed result of ECG signals and other related information, a memory for data storage, a battery for providing power, at least a contacting interface having at least one of the electrodes mounted thereon, and a detecting unit for sensing a physical condition of the contacting interface, wherein the processor compares the physical condition to a preset criterion, and takes the result as a reference for processing the ECG signals.

Here, the contacting interface can be implemented to include multiple electrodes and/or further include a structure surrounding the electrode(s) mounted thereon, and accordingly, the detecting unit can be implemented to sense the physical condition of the electrode(s) and/or the surrounding structure.

Preferably, the physical condition can be implemented to be a pressure, illumination and/or temperature, without limitation.

In an embodiment, when the physical condition is a pressure applied on the contacting interface, the detecting unit can be implemented to be a piezoelectric transducer which will convert the pressure into an electric signal for further transmitting to the processor.

In another embodiment, when the physical condition is the pressure, the detecting unit also can be implemented to be a switch, such as, a tact switch or a push button to connect to the electrode(s) and/or the surrounding structure, so as to provide a mechanical response (mechanical shift) to the force applied on the contacting interface.

Particularly, in a preferred embodiment, it can be only the surrounding structure is connected to the tact switch or the push button, so that when not in use, the electrode(s) would be lower than and protected by the surrounding structure, and only when the surrounding electrode is pressed down, the electrode can be exposed to contact the user's skin, and thus, the ECG signal acquisition can be executed. Here, by employing different switches having different operating forces, the contacting interface can be designed to respond to different applied forces, so as to conform to different requirements.

In another embodiment in which the illumination is used as the physical condition, the detecting unit, e.g., a light sensor, may detect if the electrode is sufficiently covered by the skin. In still another embodiment, the physical condition can be defined as the temperature, so that the detecting unit can sense the temperature at the surface of the electrode for contacting the skin, so as to identify the contacted situation.

It is preferable that when the physical condition matches the preset criterion, the processor directly starts the ECG signal acquisition, that is, the device can be directly initiated due to a proper contact without further pressing the "START" button. Therefore, the user can manipulate the device more conveniently.

Then, if the preset criterion is not matched, then there may be several situations. In one situation, the processor may just stop the ECG signal acquisition. In another situation, the processor may simply save the obtained raw ECG signals without any signal processing. In a further situation, the processor may mark the ECG signals for reminding the user or for further processing. In still another situation, the processor may allow the ECG signal acquisition to start and execute an alternative process to the ECG signals when the physical condition does not fall in a range for a proper acquisition.

Furthermore, in another aspect of the present invention, the detecting unit, which is connected to the interface for contacting the user's skin, also can be implemented to detect a pressure between the contacting interface and the user's skin and alter a physical condition thereof when the detected pressure matches a preset criterion, so as to conduct the circuitry for the ECG signal acquisition. That is, the circuitry for acquiring ECG signals is disconnected when there is no force applied on the contacting interface. Then, if the force applied achieves a pressure sufficient to alter the physical condition of the detecting unit, the circuitry can be conducted to become capable of performing the ECG signal acquisition.

In a preferred embodiment, the detecting unit can be implemented to be a switch, such as, a tact switch or a push button, so that when a sufficient force is applied on the electrode/surrounding structure connected thereto, it can provide a mechanical response in addition to achieving the conduction for the circuitry. And, the switch can be selected to have a desired operating force, so as to conform to the requirement difference.

Advantageously, the ECG device can further include an impedance detecting unit for sensing an impedance condition as the electrode contacts the user's skin, so as to reveal the contact condition between the electrode and the skin, for example, if there is a material which may influence the signal acquisition attached on the electrode/skin, such as, oil and sweat.

For indicating the user, it can further employ a notifying unit for being driven by the processor to send out a notification signal. Here, the notification signal can be an acoustic, a visual, and/or a tactile signal, for example, a sound, a speech, a light flash, a figure/character change, and/or a vibration, so that the user can easily and conveniently understand if a proper force is applied to contact the electrode with the skin.

Furthermore, the electrode of the ECG device can be implemented to be removable, so that the need for altering the electrode can be easily achieved. For example, a damaged electrode can be replaced, a different type of electrode can be used, e.g., a dry electrode can be exchanged to be a wet gel electrode, or an electrode mounted on the surface of the device can be replaced by a wire-connected electrode, or even the quantity of the electrodes can be varied.

In addition to the description above, the ECG device of the present invention can further include a reference electrode and/or a ground electrode which can contribute to the accuracy of examination/recording result, and an operation interface for manipulation.

Consequently, by employing a detecting unit which can detects a physical condition of the skin-contacting interface for accordingly providing the processor a reference for processing the ECG signals or for altering a physical condition itself related to the conduction for the circuitry for the ECG signal acquisition, the handheld ECG device of the present invention can determine if the contact is sufficient to perform the ECG signal acquisition, and further, during the operation, the user can clearly be indicated that if a proper electrode contact is achieved and if the ECG signal acquisition is performed correctly. Therefore, different from the conventional situation in which the correctness of ECG signal acquisition only can be checked after finishing the examination/recording, the present invention provides a more convenient and efficient way to achieve the checking in advance, which not only improves the operation procedure but also provides the reliability to the examination/recording result.

BRIEF DESCRIPTION OF THE DRAWINGS

A more detailed understanding of the invention may be had from the following description of a preferred embodiment, given by way of example, and to be understood in conjunction with the accompanying drawings, wherein.

DETAILED DESCRIPTION OF THE PREFERRED EMBODIMENTS

Figure 1:
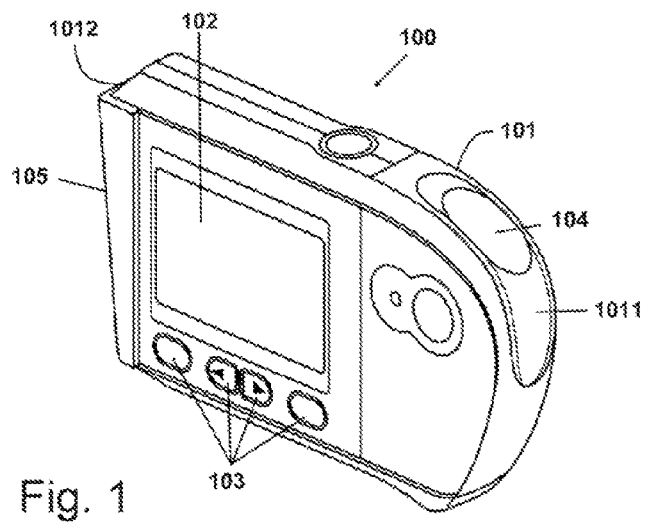
FIG. 1 is a schematic view showing a conventional handheld electrocardiographic device.
Figure 2:
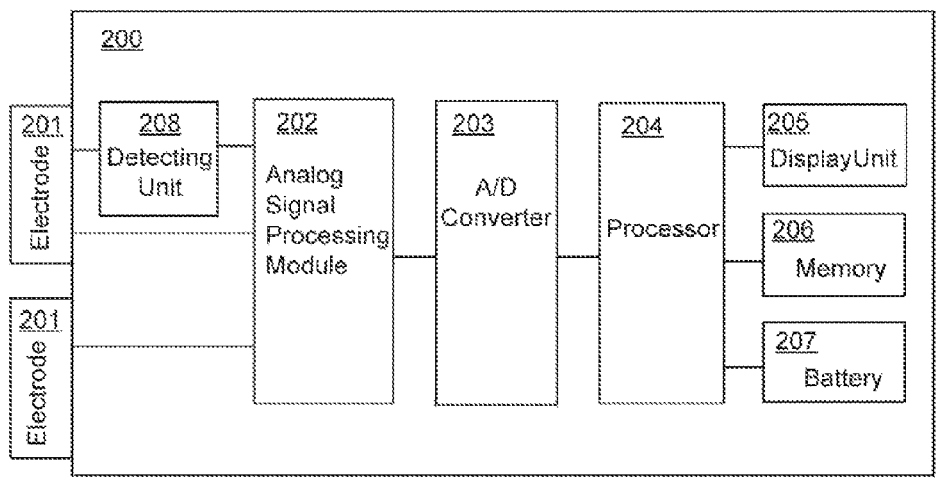
FIG. 2 is a schematic view of a handheld electrocardiographic device in a preferred embodiment of the present invention.
Figure 3:
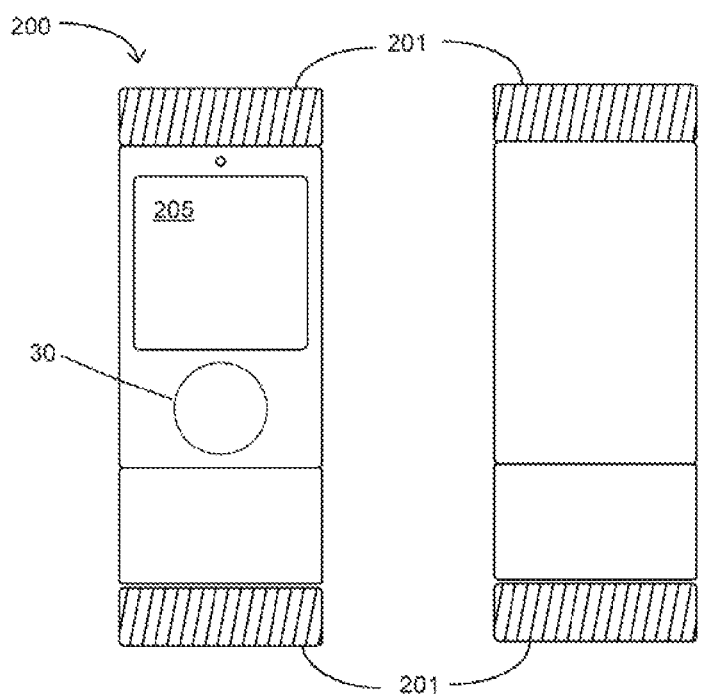
FIG. 3 shows the appearance of an exemplary handheld electrocardiographic device according to the present invention.

Please refer to FIG. 2 which is a schematic view of a handheld ECG device in a preferred embodiment of the present invention and FIG. 3 which shows the appearance of an exemplary handheld electrocardiographic device according to the present invention. As shown, the handheld ECG device 200 which is used for performing an ECG signal acquisition includes at least two electrodes 201, an analog signal processing module 202, an analog/digital converter 203, a processor 204, a display unit 205, a memory 206, a battery 207, and a detecting unit 208. The electrodes are used to obtain ECG signals from the user's skin, the analog signal processing module 202 is used to process the obtained analog ECG signals, the analog/digital converter 203 digitizes the ECG signals, the processor 204, which is the control center of the ECG device, processes the ECG signals, the display unit 205 displays a processed result of ECG signals and other related information, and the memory 206 is used for storing data.

Figure 6:
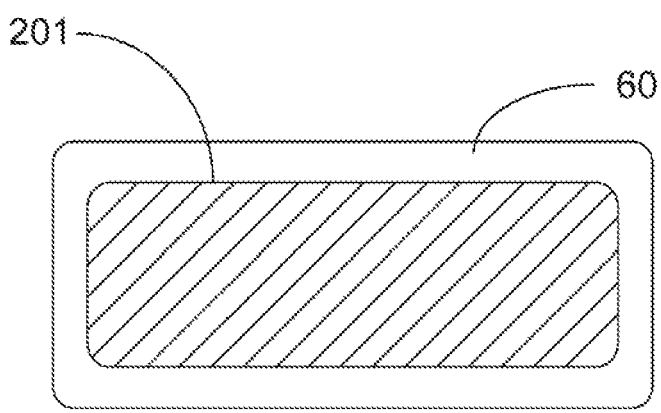
FIG. 6 is a top view of a contacting interface including an electrode with a structure surrounding said electrode according to an embodiment of the present invention.

Further, in the ECG device of the present invention, at least a contacting interface having at least one electrode 201 mounted thereon is further provided, and during the ECG signal acquisition, the contacting interface will be contacted with the user's skin, so as to allow the electrode thereon to obtain ECG signals. Then, the detecting unit 208 is implemented to sense a physical condition of the contacting interface, so that the processor 204 can compare the physical condition with a preset criterion and then take the result as a reference for processing the ECG signals. Here, the contacting interface can be implemented to include multiple electrodes 201 and/or to further include a structure 60 surrounding the electrode(s) (as shown in FIG. 6).

Figure 4A:
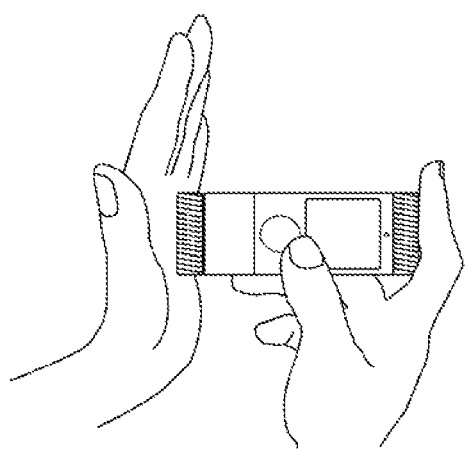
FIGS. 4A-4B are schematic views showing the usages of the handheld electrocardiographic device according to the present invention.
Figure 4B:
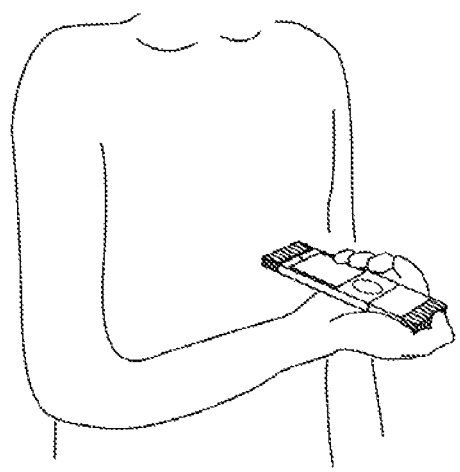
Figure 5:
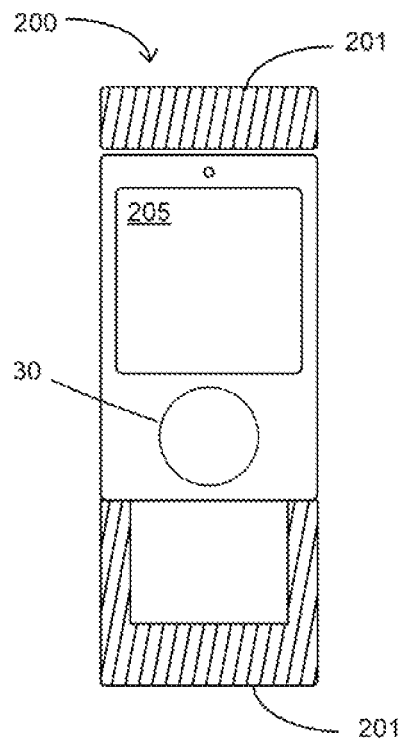
FIG. 5 shows the appearance of another exemplary handheld electrocardiographic device according to the present invention.

As shown in FIG. 3, the handheld ECG device 200 of the present invention has the electrodes 201 mounted on the surfaces thereof so as to facilitate the holding during examination/recording. In this embodiment, the electrodes 201 are respectively mounted at the two ends of the device, so that one can be contacted with the holding hand and the other can be contacted with the other skin portion, such as, the other hand (as shown in FIG. 4A) or the chest (as shown in FIG. 4B). Alternatively, in another embodiment of FIG. 5, the electrode 201 also can cover three surfaces of the device to provide another holding manner. Therefore, the arrangement of electrodes on the device's surface can be varied in accordance with different using requirements, without limitation.

Moreover, the type of the electrodes also can be different. For example, it can be implemented to be dry electrodes, wet gel electrodes and/or other suitable type of electrodes, depending on the physiological condition and the using habit etc. Plus, other than the basic two electrodes, the quantity of the electrodes also can be increased, for example, the reference electrode and/or ground electrode can be increased to reduce the noise and improve the accuracy, there is no limitation. It only needs to ensure that the additional electrode is also located at a position that can contact with the skin.

Furthermore, the electrodes also can be implemented to be removable for facilitating an exchange thereof, so as to provide the user the selectivity and convenience. For example, a dry electrode can be exchanged by a wet gel electrode to respond to different demands, an electrode mounted on the device's surface can be exchanged to be a wire-connected electrode for expanding the function of the device, or a damaged electrode can be replaced for avoiding from the abundance of the whole device. And, through the removable design, the quantity of the electrodes also can be varied, for example, the position originally for one electrode can be replaced by two smaller electrodes or a connector for multiple electrodes, without limitation.

Particularly, compared to the prior art, for reducing the error and/or failure of examination/recording caused by the insufficient contact between the electrode(s) and the skin, the present invention further employs the detecting unit 208 to connect to the contacting interface, so that a physical condition of the contacting interface as being contacted with the skin, such as, the pressure, can be detected.

The main purpose for employing the detecting unit 208 is to know if the contact between the electrode and the skin is good enough. Therefore, since the force application for maintaining the contact of the electrode with the skin decides the contact area and stability which influence the ECG signal acquisition, one way to realize if the applied force is high enough is to detect the pressure applied on the contacting interface. Thus, in a preferred embodiment of detecting the pressure, the detecting unit 208 can be implemented to be a piezoelectric transducer, so that the force applied on the contacting interface can be detected and transformed into electric signals for transmitting to the processor 204 to decide if a preset pressure range is achieved.

Figure 7:
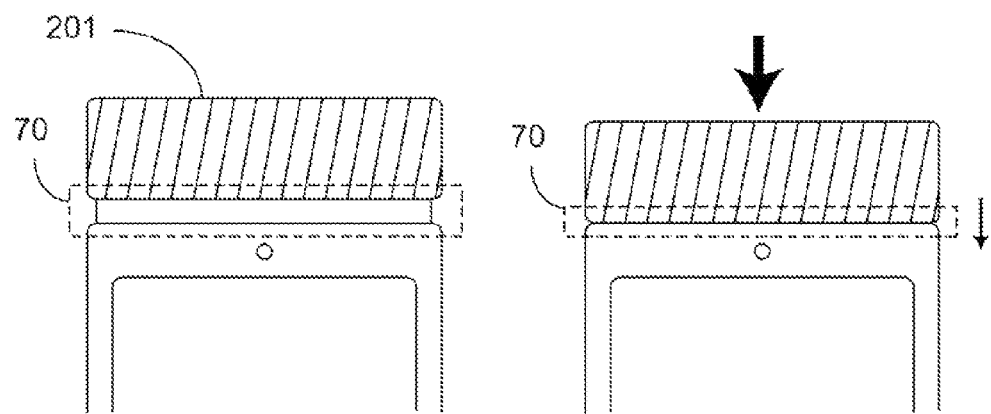
FIG. 7 is an enlarged view showing the mechanical shift of the contacting interface according to an embodiment of the present invention.

In another preferred embodiment, the detecting unit 208 also can be implemented to be a switch, such as, a tact switch or a push button, for sensing the pressure applied on the contacting interface. Through employing the tact switch or the push button, the contacting interface can have a mechanical shift 70 responding to the force applied (as shown in FIG. 7), so that the user can be indicated more positively. In practice, the switch can be connected to the electrode and/or the structure surrounding the electrode. When being connected to the electrode, the electrode will be pressed down during the examination/recording. Particularly, when the switch is connected only to the surrounding structure, the electrode will ordinarily be lower than and protected by the surrounding structure and exposed only when the surrounding structure is pressed down. Here, the detecting unit 208 can be implemented to be only one switch or a set of switches connected to the contacting interface for sensing the pressure, without limitation. Besides, owing to the feature of the switch, the contacting interface can be designed to respond to different applied forces by employing different switches having different operating forces, such as, 160 gf or 260 gf, so as to conform to different requirements.

In addition to detecting the pressure, the detecting unit 208 also can be implemented to detect other physical conditions without limitation, such as, an illumination or a temperature. For example, as detecting the illumination, a light sensor can tell that if the surface of the electrode is covered by the skin, and for detecting the temperature, a thermometer can used to measure the temperature at the electrode's surface so as to realize if the skin is already contacted with the electrode.

Noted that it can be implemented to be each contacting interface (including the reference and ground electrodes) connected with one detecting unit 208, or selectively, only one or more contacting interfaces are connected with the detecting unit(s) 208, for adapting to different requirements. Thus, there is no limitation.

Then, the processor 204 will compare the physical condition with the preset criterion, and process the ECG signals based on the comparison result. Here, the processing for the ECG signals can include, but not limited, filtering, applying an algorithm, calculating the result, and other digital signal processing. When the physical condition falls within the preset criterion, the processor 204 can allow the ECG signal acquisition to start and, more advantageously, the processor may directly initiate the acquisition without further pressing the "START" button. On the other hand, if the preset criterion is not matched, the processor 204 may process the ECG signals in several ways. For example, in one embodiment, the processor 204 may directly stop the ECG signal acquisition. In another embodiment, the processor 204 will assume that this is not a proper acquisition, and just save the raw ECG signals without any signal processing. In a further embodiment, the processor 204 may execute an alternative process to the ECG signals, e.g., applying a different algorithm, for adapting to this unmatched situation. In further another embodiment, the processor 204 may mark the ECG signals for reminding the user or for further processing. Thus, there is no limitation.

Therefore, through employing the detecting unit 208 to understand the physical condition of the contacting interface (the electrode and/or the surrounding structure) (e.g., the pressure applied thereon) as being contacted with the skin, it can assure a more proper contact between the electrode and the skin, and thus, a more correct ECG signal acquisition, compared to the prior art.

Figure 8:
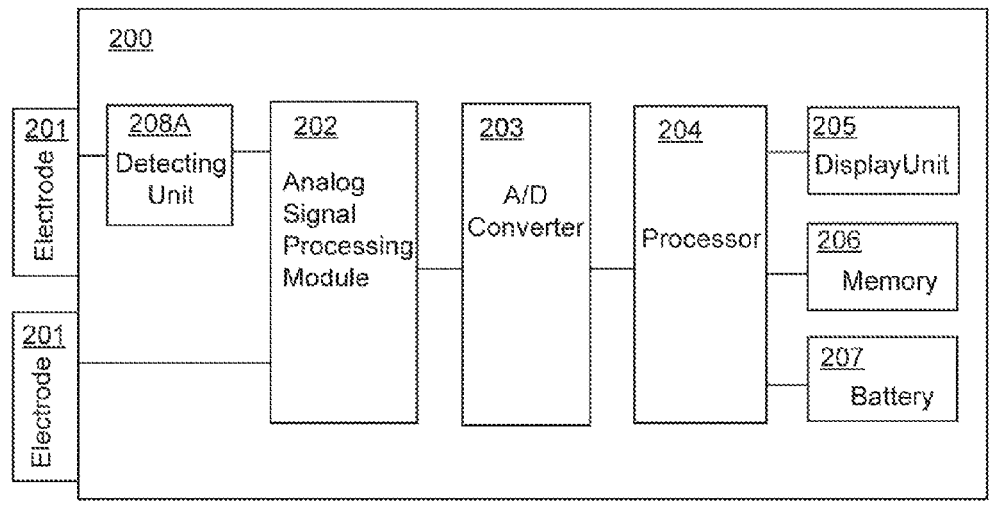
FIG. 8 is a schematic view of a handheld electrocardiographic device in another preferred embodiment of the present invention.

Furthermore, please refer to FIG. 8 showing another preferred embodiment of the present invention. In this embodiment, the detecting unit 208A is implemented to detect the pressure for contacting the contacting interface with the skin, and more particularly, the detecting unit 208A can alter a physical condition itself when the detected pressure matches a preset criterion. Here, as shown in FIG. 8, the detecting unit 208A is connected between the electrode 201 and the analog signal processing module 202, so that, particularly, the alternation of the physical condition of the detecting unit 208A is related to the conduction of the circuitry for ECG signal acquisition. That is, the alternation thereof can convert the circuitry from a disconnection status to a conducted status, so as to permit the execution of the ECG signal acquisition. For example, the detecting unit 208A can be a switch (such as, a tact switch or a push button) having a minimum triggering pressure, that is, the lower level for maintaining a proper contact between the electrode(s) and the skin and thus the examination/recording. Therefore, when the pressure higher than the lower level is applied to achieve the alternation of the physical condition, the ECG signal acquisition is accordingly allowed due to the conduction of the circuitry, that is, the user can not use the ECG device to perform the examination/recording until the physical condition of the detecting unit 208A is altered. Besides, the switch can be selected to have a desired operating force, e.g., 160 gf or 260 gf, so as to conform to the requirement difference.

Consequently, through the detecting unit 208, 208A, a proper contact between the contacting interface (the electrode) and the skin can be identified, so as to reduce the error and/or failure during the examination/recording.

Furthermore, in addition to the detecting unit, an impedance detecting unit (not shown) also can be employed to detect an impedance condition as the electrode is contacted with the skin. When the ECG signals are acquired by contact-typed electrodes, the contact condition between the electrode and the skin also influence a lot, for example, the oil, sweat, or other foreign materials on the skin surface, or a thick cuticle of the skin might degrade the signal acquisition, so that by the impedance detecting unit, these situations can be reflected on the impedance value. Therefore, if an impedance checking can be executed before the signal acquisition, it can reminder the user that the contact is not in an optimum state, and thus, the user can react promptly, such as, re-clean the skin surface or the electrode surface, for avoiding the error and/or failure.

Besides, for convenience, a notifying unit (not shown) can be further provided to notify the user the information about the contact condition between the contacting interface (the electrode) and the skin. When the processor makes any decision based on the detected physical condition, for example, if the contact is good enough, if the acquisition is initiated, if the circuitry is switched on, and/or if the alternative process is executed, the notifying unit will be driven to notify the user these decisions.

Here, the notification signal can be a visual, an acoustic and/or a tactile signal, e.g., a vibration, a light flash, a sound, a speech, characters and/or figures on the display, or a change of indicator, there is no limitation. It is important that the notification signal should let the user understand the operation situations in a clear and rapid way, for example, a proper contact is achieved, the ECG signal acquisition is going to start, the contact force is insufficient, the ECG signal acquisition can not be initiated, the ECG signal acquisition is interrupted, and/or the operation is incorrect, so that the user will not waste time on an improper signal acquisition. Therefore, there is not limitation to the implementation of the notification signal.

The display unit 205 can be implemented to show information related to the ECG signal acquisition (such as, heartbeat, heart rate, and analysis result), information about electrode contact (such as, shown by characters and/or figures), and information related to device operation (such as, time and the battery capacity), without limitation.

In addition, the memory 206 for data storage, such as, a flash memory, can be implemented to be removable, e.g., a memory card, so as to facilitate the user to provide the data to the doctor for further analysis and diagnosis. Of course, an operation interface 30 is also provided for manipulation convenience, for example, a power key, arrow keys, and an enter key, without limitation.

In the aforesaid, by employing a detecting unit which can respond to a physical condition of the contacting interface to provide the processor a reference for processing the acquired ECG signals or to provide a physical condition itself related to the conduction for the circuitry for the ECG signal acquisition, the handheld ECG device of the present invention can determine if the contact is sufficient to perform the ECG signal acquisition, so that during the operation, the user can clearly understand that if a proper electrode contact is achieved and if the ECG signal acquisition is performed correctly, thereby providing the user a convenient and efficient way to use the ECG device. Therefore, different from the conventional situation that the correctness of signal acquisition only can be checked after finishing the examination/recording, the present invention provides an effective way to achieve the checking in advance, which not only improves the operation procedure but also provides the reliability for the examination/recording result.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A handheld ECG (electrocardiographic) device for performing an ECG signal acquisition, comprising:
    at least two electrodes, for obtaining ECG signals from a user's skin;
    an analog signal processing module;
    an analog/digital converter, for digitizing the ECG signals;
    a processor, which controls the ECG device and processes the ECG signals;
    a display unit, for displaying a processed result of ECG signals and other related information;
    a memory for data storage;
    a battery, for providing power;
    at least a contacting interface, having at least one of the electrodes mounted thereon; and
    a detecting unit, continuously sensing a physical condition of the contacting interface to be an input to the processor while acquiring the ECG signals,
    wherein the processor compares the inputted physical condition with a preset criterion, and then takes the comparison result as a reference for processing the acquired ECG signals.

2. The device as claimed in claim 1, wherein the physical condition is a pressure, illumination and/or temperature.

3. The device as claimed in claim 1, wherein the contacting interface further comprises a structure surrounding the electrode mounted thereon.

4. The device as claimed in claim 3, wherein the detecting unit senses the physical condition of the electrode and/or the surrounding structure.

5. The device as claimed in claim 1, wherein the detecting unit is implemented to be a tact switch or a push button.

6. The device as claimed in claim 1, wherein the detecting unit is implemented as a piezoelectric transducer for converting a pressure on the contacting interface into an electric signal so as to be the reference for the processor to process the ECG signals.

7. The device as claimed in claim 1, wherein when the physical condition matches the preset criterion, the processor starts the ECG signals acquisition.

8. The device as claimed in claim 1, wherein when the physical condition does not match the preset criterion, the processor stops the ECG signals acquisition.

9. The device as claimed in claim 1, wherein when the physical condition does not match the preset criterion, the processor receives and saves the obtained ECG signal without further processing.

10. The device as claimed in claim 1, wherein when the physical condition does not match the preset criterion, the processor executes an alternative process to the ECG signals.

11. The device as claimed in claim 1, wherein when the physical condition does not match the preset criterion, the processor marks the ECG signals for reminding the user and/or for further processing.

12. The device as claimed in claim 1, further comprising an impedance detecting unit, for sensing an impedance condition between the electrode and the user's skin.

13. The device as claimed in claim 1, further comprising a notifying unit for being driven by the processor to send out a notification signal to notify the user the information of a contact condition between the contacting interface and the user's skin.

14. The device as claimed in claim 13, wherein the notification signal is an acoustic, a visual, and/or a tactile signal.

15. The device as claimed in claim 1, wherein at least one of the electrodes is implemented to be removable for being exchanged.

16. The device as claimed in claim 1, wherein the electrodes are implemented to be dry electrodes and/or wet gel electrodes.

17. A handheld ECG (electrocardiographic) device for performing an ECG signal acquisition, comprising:
   at least two electrodes, for obtaining ECG signals from a user's skin;
   an analog signal processing module;
   an analog/digital converter, for digitizing the ECG signals;
   a processor, which controls the ECG device and processes the ECG signals;
   a display unit, for displaying a processed result of ECG signals and other related information;
   a memory, for data storage;
   a battery, for providing power;
   at least a contacting interface, having at least one of the electrodes mounted thereon; and
   a detecting unit, connected to the contacting interface,
   wherein the detecting unit detects a pressure for contacting said contacting interface to the user's skin, and alters a physical condition thereof when the detected pressure matches a preset criterion, so as to conduct the circuitry for ECG signal acquisition; and
   a notifying signal is further generated and employed, during the ECG signal acquisition, to notify the user of a contact condition between the contacting interface and the user's skin when the detected pressure matches the preset criterion.

18. The device as claimed in claim 17, wherein the contacting interface further comprises a structure surrounding the electrode mounted thereon.

19. The device as claimed in claim 18, wherein the detecting unit is connected to the electrode and/or the surrounding structure.

20. The device as claimed in claim 17, wherein the detecting unit is implemented to be a tact switch or a push button.

* * * * *